United States Patent [19]

Chang et al.

[11] Patent Number: 4,849,224

[45] Date of Patent: Jul. 18, 1989

[54] DEVICE FOR ADMINISTERING AN ACTIVE AGENT TO THE SKIN OR MUCOSA

[75] Inventors: Yunik Chang, Toms River, N.J.; Dinesh C. Patel, Murray; Charles D. Ebert, Salt Lake City, both of Utah

[73] Assignee: TheraTech Inc., Salt Lake City, Utah

[21] Appl. No.: 119,617

[22] Filed: Nov. 12, 1987

[51] Int. Cl.⁴ .............................................. A61F 13/00
[52] U.S. Cl. .................................. 424/434; 424/448; 424/449
[58] Field of Search ............... 424/434, 447, 448, 449; 604/304, 307, 897

[56] References Cited

U.S. PATENT DOCUMENTS

| | | | |
|---|---|---|---|
| 4,560,553 | 12/1985 | Zupan | 424/45 |
| 4,568,343 | 2/1986 | Leeper et al. | 514/552 |
| 4,573,996 | 3/1986 | Kwiatek et al. | |
| 4,637,930 | 1/1987 | Konno et al. | 604/304 |
| 4,655,767 | 4/1987 | Woodward et al. | 424/448 |
| 4,687,481 | 8/1987 | Nuwayser | 424/449 |
| 4,690,683 | 9/1987 | Chien et al. | 424/448 |
| 4,695,277 | 9/1987 | Lauk | 604/304 |
| 4,704,119 | 11/1987 | Shaw et al. | 424/449 |
| 4,710,191 | 12/1987 | Kwiatek et al. | |
| 4,747,841 | 5/1988 | Kuratomi et al. | 424/447 X |
| 4,764,379 | 8/1988 | Sanders et al. | 424/448 X |

Primary Examiner—Nancy A. B. Swisher

[57] ABSTRACT

A transdermal drug delivery device comprising a drug formulation-containing reservoir defined by a backing layer and a drug-permeable membrane layer, a ring-shaped layer made of an adhesive that is incompatible with one or more components of the drug formulation that is peripheral to the reservoir outwardly of the membrane layer and a peelable liner layer that underlies at least the membrane layer with a first heat seal between the backing and the membrane about the perimeter of the reservoir and another concentric heat seal between the backing and the release liner positioned outwardly of the first heat seal, the heat seals providing barriers that isolate the drug formulation from the adhesive.

7 Claims, 2 Drawing Sheets

DEVICE FOR ADMINISTERING AN ACTIVE AGENT TO THE SKIN OR MUCOSA

TECHNICAL FIELD

This invention is in the field of transdermal/transmucosal administration of active agents (drugs). More particularly it relates to a device for achieving such administration comprising an active agent-containing reservoir and an adhesive layer for affixing the device to the skin or mucosa in which the adhesive layer is peripheral to the path of the active agent to the skin or mucosa and is protected from degradation by the components of the reservoir by a multiplicity of heat seals.

BACKGROUND OF THE INVENTION

There are many patents describing devices for administering drugs through the skin or mucosa. These devices are commonly in the form of a laminated composite that includes a reservoir layer containing the drug, a pressure sensitive adhesive layer for attaching the composite to the skin, and a backing layer that forms the upper layer of the device. Depending upon the particular drug and drug formulation involved, the reservoir layer may be a matrix in which the drug formulation is dispersed or a layer in the form of a walled container which holds the drug formulation. Container-type reservoirs are often formed as a pocket between the backing layer and a drug-permeable basal membrane through which the drug passes to the skin. The pressure sensitive adhesive layer normally underlies the membrane and the drug also passes through it on its way to the skin.

Devices having container type reservoirs with underlying pressure sensitive adhesive layers have significant disadvantages when one or more components of the drug formulation that are released from the reservoir to the skin are solvents for the adhesive or otherwise adversely effect the properties of the adhesive as they pass through it to the skin. In such cases those reservoir component(s) cannot be permitted to pass through the adhesive and means must be found to isolate the adhesive from them. The present invention provides a device design in which the adhesive is peripheral to the path of the drug formulation and is isolated from the drug formulation by a multiplicity of heat seals between selected layers of the device.

At least one other transdermal drug delivery device design has been proposed which involves an adhesive layer that is peripheral to the path of the drug to the skin. U.S. Pat. No. 4,573,996 describes a device that has both a drug-permeable adhesive layer in the path of the drug and a peripheral drug-impermeable adhesive layer that is not in the path of the drug. The purpose of the peripheral adhesive layer is to provide a site for handling the device which avoids the risks of effecting the drug path or contaminating the fingers with drug. FIG. 6 of the patent shows a multi-layer laminated composite composed of (1) a backing layer, (2) a drug permeable membrane underlying the backing that forms with the backing a pocket that serves as a drug-containing reservoir, (3) a drug-permeable adhesive layer directly underlying the membrane (4) a ring-shaped drug-impermeable adhesive layer adjacent and peripheral to the drug-permeable adhesive layer, and (5) a basal removable protective layer. The combination of a heat seal between the backing and the membrane at the edge of the reservoir and the peripheral drug-impermeable adhesive layer prevents radial or horizontal migration of the drug from the reservoir. This patented device is distinct from the device of the present invention in several respects. The patented device does not involve the problem of keeping drug formulation components isolated from the adhesive layer. In the patented device, the drug passes through the drug-permeable adhesive layer. There is only a single heat seal shown in the patented device. And, the single heat seal is not used to isolate the drug formulation from either adhesive layer.

DISCLOSURE OF THE INVENTION

The invention is a device for administering an active agent to the skin or mucosa of an individual comprising a laminated composite of:
(a) a backing layer;
(b) an active agent-permeable membrane, the backing layer and membrane defining
(c) a reservoir therebetween that contains a formulation of the active agent;
(d) a ring-shaped adhesive layer that is peripheral to the reservoir and provides a means for attaching the device to the skin or mucosa;
(e) a removable active agent formulationimpermeable layer that covers the membrane and the adhesive layer;
(f) a first heat seal about the peripheral of the reservoir between the backing layer and the membrane; and
(g) a second heat seal outwardly of the first heat seal and inwardly of the adhesive layer between the backing layer and the removable layer, said heat seals providing barriers to migration of components of the active agent formulation from the reservoir into the adhesive layer.

BRIEF DESCRIPTION OF THE DRAWINGS

Like parts are referred to by like numerals in the drawings.

MODES FOR CARRYING OUT THE INVENTION

Figure 1:
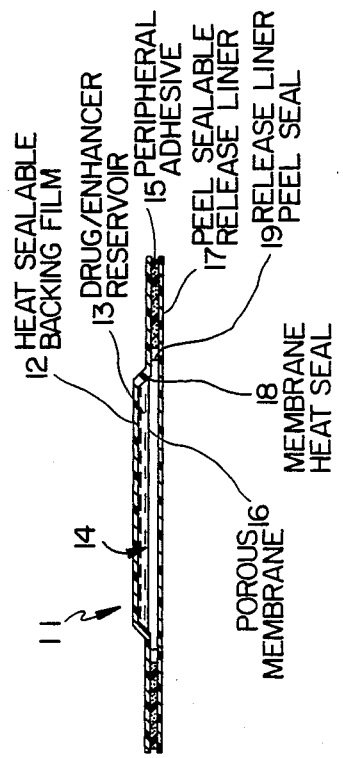
FIG. 1 is an enlarged sectional view of one embodiment of the device of the invention.

FIG. 1 shows a device, generally designated 11, that is an embodiment of the invention that is designed to administer a formulation of a drug and/or a permeation enhancer that is a solvent for pressure sensitive adhesives that are commonly used in transdermal delivery devices. Device 11 is designed to place the adhesive out of the path of enhancer-drug formulation and to prohibit radial or horizontal migration of the enhancer into the adhesive. Device 11 is a laminated composite. The uppermost layer of the composite is a heat-sealable backing film 12 having an inverted, cup-shaped recess 13 that serves as a container or reservoir for a drug-enhancer formulation 14. The underside of the outer edge of the backing film carries a ring-shaped layer 15 of a pressure sensitive adhesive peripheral to the reservoir. Underlying the reservoir and located inwardly of the peripheral ring of adhesive is a membrane layer 16 that is permeable to the drug-enhancer formulation. Finally a peel sealable release line layer 17 covers the entire underside of the assembly and forms a basal surface of the device. There are two concentric heat seals in the composite. The first is at 18 between the membrane and the backing. It extends completely around the perimeter of the reservoir and forms a permanent seal between the backing film and membrane. The second is at 19 and is between the release liner and the backing layer and forms a peel seal between the backing film and release liner. It is concentric to and outwardly of the first heat seal. These seals prevent the enhancer from migrating into the adhesive during storage. After the release liner is removed, the first heat seal prevents such migration. The width of the seals will usually be in the range of 0.1 to 1.0 cm.

Figure 2:
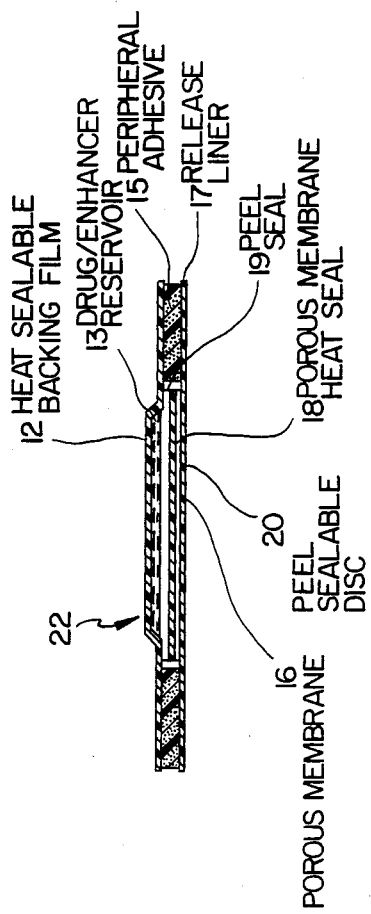
FIG. 2 is an enlarged sectional view of another embodiment of the invention.

The device of FIG. 2, generally designated 22, is similar in design to device 11. The backing film 12 of device 22 is a heat sealable material and as in device 11 the backing has a inverted cup-shaped reservoir that contains the active agent formulation, is underlayed by a microporous membrane, and has a ring-shaped layer of adhesive carried on the underside of the edge of the backing outwardly of the membrane. Unlike device 11, however, device 22 has a peel sealable inner liner 20 which underlies the microporous membrane and portions of the backing film. The release liner layer 17 covers the entire underside of the assembly and forms the basal surface of the device prior to its use. Device 22 has a heat seal 18 between the membrane and backing film 12 and a peelable (impermanent) heat seal 19 between backing film 12 and the outer perimeter of the inner liner 20. These seals are identical in location and function to the corresponding seals of device 12.

When devices 11 and 22 are placed into use, the release liner layer 17 is peeled away from the underside of the device and discarded. In the case of device 11 this operation directly exposes the undersurfaces of the membrane and the adhesive layer and the device can be placed on a desired site on the skin or mucosa of the individual to be treated with the active agent. In the case of device 22, the inner line 20 must be peeled away in order to expose the microporous membrane.

In the embodiments shown in FIGS. 1 and 2 the second heat seal is formed between the backing and release liner. It will be appreciated in this regard that additional heat-sealable layers could be included in the device that sandwich the adhesive and extend inwardly of the adhesive and that the second heat seal at the inner periphery of the adhesive could be formed between such additional layers or between such layers and the backing or release liner. In this regard such additional layers that lie above the adhesive would be considered to be part of the backing and such additional layer(s) lying below the adhesive would be considered to be part of the strippable layer that covers the basal surfaces of the adhesive and membrane.

Such devices are useful when one or more of the components of the active agent formulation is incompatible with available adhesives that are useful for removably attaching elements to the skin or mucosa. The term "incompatible" is intended to mean that through physical and/or chemical interaction of the component(s) with the adhesive the adhesiveness or other desirable properties (e.g, nonirritancy) of the adhesive are significantly destroyed or impaired. The drug itself may be such a component or a carrier, solvent, skin permeation enhancing agent or other additive may be such a component.

The backing layer 12 of the devices may be composed of a single film or a plurality of films. In any event, its inner surface must be capable of being heat sealed to the membrane and release liner layers of the device. One or more of the films that constitute the layer will be impermeable to components of the drug formulation contained in the reservoir. Examples of materials used as backing layers in transdermal delivery devices that may find use in the present invention are polyethylene, polypropylene, polyvinylchloride, polyethylene terephthalate, and combinations thereof. The layer may include one or more metal layers and/or one or more fibrous layers.

The reservoir pocket in the backing may be formed by vacuum forming or other like methods of forming desired shapes in films.

The term "drug" as used to describe the principal active ingredient of the device intends a biologically active compound or mixture of compounds that has a therapeutic, prophylactic or other beneficial pharmacological and/or physiological effect on the wearer of the device. Examples of types of drugs that may be used in the invention device are antiinflammatory drugs, analgesics, antiarthritic drugs, antispasmodics, antidepressants, antipsychotic drugs, tranquilizers, antianxiety drugs, narcotic antagonists, antiparkinsonism agents, cholinergic agonists, anticancer drugs, immunosuppression agents, antiviral agents, antibiotic agents, appetite suppressants, antiemetics, anticholinergics, antihistamines, antimigraine agents, coronary, cerebral or peripheral vasodilators, hormonal agents, contraceptive agents, antithrombotic agents, diuretics, antihypertensive agents, cardiovascular drugs, and the like. The appropriate drugs of such types are capable of permeating through the skin either inherently or by virtue of treatment of the skin with a percutaneous absorption enhancer. Because the size of the device is limited for patient acceptance reasons, the preferred drugs are those that are effective at low concentration in the blood stream. Examples of specific drugs are steroids such as estradiol, progesterone, norgestrel, levonorgestrel, norethindrone, medroxyprogestrone acetate, testosterone and their esters, nitro-compounds such as nitroglycerine and isosorbide nitrates, nicotine, chlorpheniramine, terfenadine, triprolidine, hydrocortisone, oxicam derivatives such as piroxicam, ketoprofen, mucopolysaccharidases such as thiomucase, buprenorphine, fentanyl, naloxone, codeine, dihydroergotamine, pizotiline, salbutamol, terbutaline, prostaglandins such as misoprostol and enprostil, omeprazole, imipramine, benzamides such as metoclopramine, scopolamine, peptides such as growth releasing factor and somatostatin, clonidine, dihydropyridines such as nifedipine, verapamil, ephedrine, pindolol, metoprolol, spironolactone, nicardipine hydrochloride, calcitriol, thiazides such as hydrochlorothiazide, flunarizine, sydononimines such as molsidomine, sulfated polysaccharides such as heparin fractions and the salts of such compounds with pharmaceutically acceptable acids or bases, as the case may be.

Depending upon the inherent permeability of the skin to the particular drug or drugs being administered by the device, the reservoir may also contain a percutaneous absorption enhancer that increases the permeability of the skin to the drug(s) and is coadministered to the skin. Examples of percutaneous absorption enhancers are those referred to in U.S. Pat. Nos. 3,989,816, 4,316,893, 4,405,616, 4,060,084, and 4,379,454 and J Pharm Sci (1975) 64:901-024. The formulation contained in the reservoir may also include solvent(s), gelling agents, stabilizers, and other additives. As indicated previously one or more of these components or a combination of these components is incompatible with the adhesive.

The membrane is permeable to the drug. It may be a "dense" membrane made of a material that is inherently permeable to the components of the reservoir that are to be administered to the skin or mucosa or it may be made of a microporous material whose pores are filled with a drug-permeable material. In the case of dense membranes, the component(s) dissolve in the material and diffuse through the material to the skin. In the case of microporous materials the component(s) diffuse through the pores to the skin. The membrane may or may not be a rate-controlling element depending upon the particular drug involved, the permeability of the skin to the drug, and the rate of delivery required to provide therapy. Examples of materials for making dense membranes are given in U.S. Pat. Nos. 3,598,122 and 4,650,484. Examples of materials for making microporous membranes are provided in U.S. Pat. Nos. 3,797,494 and 4,031,894.

The peripheral adhesive layer is composed of a pressure sensitive surgical adhesive such as those that are commonly used to affix transdermal drug delivery devices, bandages or other dressings to the skin. Examples of such adhesives are polyisobutene, natural rubber adhesives, acrylic and methacrylic adhesives, and silicone adhesives.

The release liner layer 17 (and inner liner 20) may be composed of a single layer or a multiplicity of layers. It should be (1) impermeable to the components of the drug formulation that diffuse through the membrane, (2) heat sealable, and (3) is inherently strippable or peelable or rendered so by techniques such as silicon or fluorocarbon treatment. An example of a film having such properties is 3M release liner MSX-899.

The respective components of the device may be formulated and assembled using procedures that are known in the drug formulation, transdermal device, and laminating arts. The shape of the device is not critical, and devices of preformed shapes may be assembled directly or punched, cut, or otherwise formed from large sheets of laminated composite.

The following examples further illustrate the invention. These examples are not intended to limit the invention in any manner.

EXAMPLES

Example 1

A membrane/peripheral adhesive/peel seal release liner laminate is prepared by casting a 35% by weight aqueous acrylic adhesive emulsion (Monsanto Gelva 2484) onto a silanized polyester release liner (Mead Release Products) using a 7.5 mil gap Gardener knife. The aqueous solvent is evaporated in an oven to yield a 2.5 mil thick adhesive coating. The adhesive/release liner is then laminated to a second silanized release liner and a 1.5 cm$^2$ circular disc is die cut from the laminate using a steel rule die. One release liner is peeled from the adhesive and a peal seal release liner (3M, MSX-899) is laminated to the exposed adhesive surface, forming laminate L1.

A gelled pindolol HCl/permeation enhancer reservoir ointment is prepared by mixing adequate quantities of a 1/1 volume ratio of isopropyl alcohol/methyl laurate with pindolol HCl and Klucel ® gelling agent (FMC) to provide a 50 mg/ml pindolol suspension containing 5% by weight Klucel ® gelling agent.

The backing film (Scotchpak 1006) is then thermal formed to provide a 10 cm$^2$ surface area, 2 cc volume cup. Two milliliters of the pindolol HCl/enhancer ointment is then pipetted into the dimpled cup and a 2 mil thick microporous polyethylene membrane (3M, MSX-894) is heat sealed around the perimeter of the drug reservoir cup at 340° C. for 0.5 seconds. Excess membrane exterior to the 10 cm$^2$ heat seal is then trimmed away. The die cut release liner of laminate L1 is removed and the adhesive surface is laminated to the backing film, the 15 cm$^2$ die cut area of the adhesive positioned concentrically around the 10 cm$^2$ membrane sealed reservoir cup. The backing film is then sealed to the outer peel seal release liner at 350° C. for 0.5 seconds within the 15 cm$^2$ relief area of the die cut adhesive zone, producing a heat seal ring, 12.5 cm$^2$ surface concentric with the drug reservoir. All heat seals, 10 cm$^2$ backing film to membrane, and 12.5 cm$^2$ backing film to release liner are 0.1 cm wide. A permanent heat seal is formed between the backing film and the microporous membrane, while a peel seal is formed between the backing film and release liner. Final systems are then die cut using a 30 cm$^2$ circular steel rule die. Systems are then pouched in paper/aluminum foil/polyethylene pouches.

Example 2

A 30% by weight polyisobutene (PIB) adhesive in heptane is cast on a silanized release liner using a 10 mil gap Gardener knife. The solvent is evaporated to yield a 2.0 mil thick PIB adhesive layer. A 15 cm$^2$ circular disc is die cut from a 1.0 mil thick peel seal release liner (3M, MSX-899) and laminated to the PIB adhesive with the peel seal release surface facing out from the adhesive surface, forming laminate L1. The backing film (Scotchpak 1012) is dimpled as described in Example 1 to form a 10 cm$^2$ surface area, 2 cc volume cup. Pindolol/enhancer reservoir gel, prepared as described in Example 1, is pipetted (2 cc) into the cup and a 1.0 mil microporous polyethylene membrane (Questar, K-861) is heat sealed around the drug reservoir cup as described in Example 1. The PIB surface of laminate L1 is then laminated to the backing film such that the 15 cm$^2$ peel seal disc concentrically overlaps the 10 cm$^2$ drug reservoir cup. The backing film is then sealed to the peel seal disc of laminate L1 to form a heat seal ring, 12.5 cm$^2$ concentric with the 10 cm$^2$ drug reservoir. All heat seals are 0.1 cm wide. Final 30 cm$^2$ circular shaped systems are then die cut and pouched as described in Example 1.

The 10 cm$^2$ heat seal forms a permanent seal between the backing film and the microporous membrane, thus forming the drug/enhancer reservoir. The peel seal formed between the backing film and the release liner then prevent drug/enhancer migration from the reservoir into the peripheral adhesive. As long as the peel strengths between the (1) release liner and the PIB adhesive and, (2) the PIB adhesive and the 15 cm$^2$ peel seal disc are greater than the force necessary to separate the peel seal between the backing film and the 15 cm$^2$ peel seal disc, the peel seal disc will be removed from the system leaving the peripheral adhesive on the system, when the release liner is removed.

Examples 3 and 4

Transdermal drug delivery systems are prepared as described in Examples 1 and 2 using a Nicardipine HCl/enhancer reservoir gel prepared by adding Nicardipine HCl and Klucel® to a 3/2 volume ratio of isopropanol/methyl laurate in quantities sufficient to provide a 50 mg/ml Nicardipine HCl suspension concentration with 4.5% by weight Klucel®, in place of the pindolol HCl/enhancer reservoir gel. The in vitro, steady state transdermal flux of Nicardipine HCl across human cadaver skin was determined using the methods of Merritt and Cooper (*J Controlled Release* (1984) 1:161), to be 3 ug-cm$^2$/hr.

Examples 5 and 6

Transdermal drug delivery systems are prepared as described in Examples 1 and 2 using a Calcitriol/enhancer reservoir gel, prepared by mixing sufficient amounts of Calcitriol and Klucel® with a 71%/4%/25% ethanol/methyl laurate/water tri-solvent mixture to provide a 100 ug/ml Calcitriol concentration with an 8.7% by weight Klucel® level, in place of the pindolol HCl/enhancer gel. The in vitro, steady state transdermal flux of Calcitriol across human cadaver skin was determined using the methods of Merritt and Cooper (*J Controlled Release* (1984) 1:161),to be 0.67 ug/cm$^2$/day.

Modifications of the above described modes for carrying out the invention that are obvious to those of skill in the fields of pharmaceutical chemistry, transdermal drug delivery, or related fields are intended to be within the scope of the following claims.

We claim:

1. A device for administering an active agent to the skin or mucosa of an individual comprising a laminated composite of:
   (a) a backing layer;
   (b) an active agent-permeable membrane, the backing layer and membrane defining
   (c) a reservoir therebetween that contains a formulation of the active agent, said reservoir having a smaller periphery than the backing layer and membrane such that a portion of the backing layer and membrane extends outwardly of the periphery of the reservoir;
   (d) a first peelable active agent formulation-impermeable layer that underlies the reservoir and a portion of said outwardly extending portion of the backing layer and membrane;
   (e) an adhesive layer that underlies and covers the first peelable active agent formulation-impermeable layer and said outwardly extending portion of the backing layer and membrane;
   (f) a second peelable active agent formulation-impermeable layer that underlies and covers the adhesive layer;
   (g) a permanent heat seal about the periphery of the reservoir between the backing layer and the membrane; and
   (h) a peelable heat seal outwardly of the permanent heat seal between the backing and the first peelable active agent formulation-impermeable layer, the peel strengths between the adhesive layer and the first and second peelable active agent impermeable layers being greater than the force required to break the peelable heat seal whereby when the second peelable layer is removed from the device, the peelable heat seal is broken and the first peelable layer and underlying portion of the adhesive layer is removed therewith.

2. The device of claim 1 wherein the adhesive is incompatible with one or more of the components of the formulation that permeate through the membrane to the skin or mucosa.

3. The device of claim 1 wherein the backing layer is a laminated composite of at least one layer that is impermeable to the formulation and an inner heat-sealable layer.

4. The device of claim wherein the adhesive is an acrylic adhesive, the active agent is pindolol hydrochloride, and the formulation includes isopropyl alcohol and methyl laurate.

5. The device of claim 4 wherein the membrane is a microporous polyethylene membrane.

6. The device of claim 1 wherein the adhesive is an acrylic adhesive, the active agent is nicardipine hydrochloride, and the formulation includes isopropyl alcohol and methyl laurate.

7. The device of claim 1 wherein the adhesive is an acrylic adhesive, the active agent is calcitriol and the formulation includes ethanol, methyl laurate, and water.

* * * * *